US009241973B2

(12) United States Patent
Suh et al.

(10) Patent No.: US 9,241,973 B2
(45) Date of Patent: Jan. 26, 2016

(54) COMPOSITION FOR TREATMENT OR PREVENTION OF ERECTILE DYSFUNCTION INCLUDING DKK2 PROTEIN OR DKK2 GENE THEREOF AND USE OF THE COMPOSITION

(75) Inventors: Jun Kyu Suh, Seoul (KR); Ji Kan Ryu, Incheon (KR); Hai Rong Jin, Incheon (KR); Young Guen Kwon, Seoul (KR)

(73) Assignee: INHA INDUSTRY PARTNERSHIP INSTITUTE, Incheon (KR)

( * ) Notice: Subject to any disclaimer, the term of this patent is extended or adjusted under 35 U.S.C. 154(b) by 0 days.

(21) Appl. No.: 14/233,378

(22) PCT Filed: Apr. 10, 2012

(86) PCT No.: PCT/KR2012/002734
§ 371 (c)(1),
(2), (4) Date: Jan. 16, 2014

(87) PCT Pub. No.: WO2013/027911
PCT Pub. Date: Feb. 28, 2013

(65) Prior Publication Data
US 2014/0235527 A1    Aug. 21, 2014

(30) Foreign Application Priority Data

Aug. 22, 2011  (KR) .................. 10-2011-0083560
Mar. 15, 2012  (KR) .................. 10-2012-0026614

(51) Int. Cl.
*A61K 38/17*    (2006.01)
*A61K 9/00*     (2006.01)

(52) U.S. Cl.
CPC ............... *A61K 38/17* (2013.01); *A61K 9/0019* (2013.01); *A61K 9/0034* (2013.01)

(58) Field of Classification Search
CPC .... C07K 14/47; C07K 14/4703; A61K 38/00; A61K 48/00; A61K 38/17; A61K 38/1709; A61K 48/005; A61K 48/0075; A61K 38/1891; A61K 9/0034; A61K 9/0019; G01N 33/5041; A01K 2217/052; A01K 2217/206; A01K 2227/105; A01K 2267/0362; A01K 2267/0375; A01K 67/0275; C12N 2799/022
See application file for complete search history.

(56) References Cited

U.S. PATENT DOCUMENTS

2002/0032153 A1* 3/2002 Whitehouse .................... 514/12
2011/0223184 A1* 9/2011 Kwon et al. ................. 424/178.1

FOREIGN PATENT DOCUMENTS

WO   WO 0052047 A2 *  9/2000    ............ C07K 14/47
WO       2007/136226 A1    11/2007

OTHER PUBLICATIONS

UniProt Protein Database, Q9UBU2 (DKK2_HUMAN), Dickkopf-related protein 2, amino acid sequence on p. 3, accessed on Aug. 12, 2014.*
Ji-Kan Ryu, Combined Angiopoietin-1 and Vascular Endothelial Growth Factor Gene Transfer Restores Cavernous Angiogenesis and Erectile Function in a Rat Model of Hypercholesterolemia, Molecular Therapy vol. 13, No. 4, Apr. 2006.*
Jin HR, Intracavernous delivery of synthetic angiopoietin-1 protein as a novel therapeutic strategy for erectile dysfunction in the type II diabetic db/db mouse, J Sex Med. Nov. 2010;7(11):3635-46, Abstract.*
Choi, "Development of method of treatment using an epoch-making angiogenesis factor, DKK2," *Doctor's News*, downloaded at www.doctorsnews.co.kr/news/articleView.html?idxno=69645 (Apr. 11, 2011).
Krupnik, et al., "Functional and structural diversity of the human Dickkopf gene family," *Gene*, vol. 238(2), pp. 301-313 (1999).
Li, et al., "Dkk2 has a role in terminal osteoblast differentiation and mineralized matrix formation," *Nat. Genet.*, vol. 37(9), pp. 945-952 (2005).
Lysiak, et al., "Angiogenesis therapy for the treatment of erectile dysfunction," *J. Sex. Med.*, vol. 7, No. 7, pp. 2554-2563 (Jul. 2010).
Min, et al., "The WNT antagonist Dickkopf2 promotes angiogenesis in rodent and human endothelial cells", *J. Clin. Invest.*, vol. 121, No. 5, pp. 1882-1893 (May 2011).
Wu, et al., Mutual antagonism between *dickkopf1* and *dickkopf2* regulates Wnt/β-catenin signalling, *Curr. Biol.*, vol. 10(24), pp. 1611-1614 (2000).
International Search Report for International Application No. PCT/KR2012/002734, mailed Oct. 23, 2012.
Written Opinion for International Application No. PCT/KR2012/002734, mailed Oct. 23, 2012.
Ryu et al., "Transforming growth factor-β type I receptor inhibitor induces functional and morphologic recovery in a rat model of erectile dysfunction and cavernous fibrosis", *Korean J Androl.*, 30(1): 23-30 (Apr. 2012).
Park et al., "Effects of Intracavernosal IGF-1 gene delivery on erectile function in the aging rat", *Korean Journal of Urology*, 46:406-413 (2005).
Pu et al., "Insulin-Like growth factor-1 restores erectile function in aged rats: modulation the integrity of smooth muscle and nitric oxide-cyclic guanosine monophosphate signaling activity", *J Sex Med.*, 5:1345-1354 (2008).
Celletti et al., "Vascular endothelial growth factor enhances atherosclerotic plaque progression", *Nature Medicine*, 7(4) 425-429 (Apr. 2001).
Ferrara et al., "The biology of VEGF and its receptors", *Nature Medicine*, 9(6): 669-76 (Jun. 2003).
Proescholdt et al., "Vascular endothelial growth factor (VEGF) modulates vascular permeability and inflammation in rat brain", *J Nuropathology and Experimental Neurology*, 58(6): 613-27 (Jun. 1999).
Zhan et al., "VEGF is associated with the poor survival of patients with prostate cancer: a meta-analysis", *Transl Androl Urol*, 2(2): 99-105 (2013).

(Continued)

*Primary Examiner* — James H Alstrum Acevedo
*Assistant Examiner* — Erinne Dabkowski
(74) *Attorney, Agent, or Firm* — Kilpatrick Townsend & Stockton LLP

(57)    ABSTRACT

A pharmaceutical composition for regenerating an endothelial cell which includes as an active ingredient a DKK2 protein or a polynucleotide encoding the DKK2 protein, a pharmaceutical composition for preventing or treating erectile dysfunction, a method of regenerating an endothelial cell of a subject and a method of preventing or treating erectile dysfunction of a subject and which treat or prevent erectile dysfunction in a subject.

2 Claims, 9 Drawing Sheets

(56) References Cited

OTHER PUBLICATIONS

Shah et al., VEGF overexpression in MCF-7 breast cancer cells increases invasion and lactate production:, Proc. Intl. Soc. Mag. Reson. Med. 17(2009).

Goel et al. "VEGF targets the tumour cell", *Nature Reviews Cancer*, 13: 871-82 (Dec. 2013).

Schoeffner et al., "VEGF contributes to mammary tumor growth in transgenic mice through paracrine and autocrine mechanisms", *Laboratory Investigation*, 85, 608-23 (2005).

Hirakawa et al., "VEGF-A induces tumor and sentinel lymph node lymphangiogenesis and promotes lymphatic metastasis", *JEM*, 201(7), 1089-99 (Apr. 4, 2005).

Giri et al., "Alterations in Expression of Basic Fibroblast Growth Factor (FGF) 2 and its Receptor FGFR-1 in Human Prostate Cancer", *Clinical Cancer Research*, 5:1063-1071 (May 1999).

Zittermann et al., "Basic Fibroblast Growth Factor (bFGF, FGF-2) Potentiates Leukocyte Recruitment to Inflammation by Enhancing Endothelial Adhesion Molecule Expression", *American Journal of Pathology*, 168(3) 835-46 (Mar. 2006).

Floege et al. "Basic Fibroblast Growth Factor Augments Podocyte Injury and. Induces Glomerulosclerosis in Rats with Experimental Membranous Nephropathy", *J. Clin. Invest.*, 96,: 2809-2819 (Dec. 1995).

Polnaszek et al., "Fibroblast Growth Factor 2 Promotes Tumor Progression in an Autochthonous Mouse Model of Prostate Cancer", *Cancer Research*, 63: 5754-5760 (Sep. 15, 2003).

Gan et al., Pharmaceutical Research, vol. 23, No. 6, Jun. 2006. "Expression of Basic Fibroblast Growth Factor Correlates with Resistance to Paclitaxel in Human Patient Tumors".

Strutz et al., "Role of basic fibroblast growth factor-2 in epithelial-mesenchymal transformation", *Kidney International*, 61 : 1714-28 (2002).

\* cited by examiner

WT, wild-type C57BL mouse
DKK2-Tg, DKK2 transgenic mouse
STZ, streptozotocin

WT, wild-type C57BL mouse
DKK2-Tg, DKK2 transgenic mouse
STZ, streptozotocin

SEQUENCE LISTING

```
<160> NUMBER OF SEQ ID NOS: 7

<210> SEQ ID NO 1
<211> LENGTH: 259
<212> TYPE: PRT
```

-continued

```
<213> ORGANISM: Homo sapiens
<220> FEATURE:
<223> OTHER INFORMATION: Dickkopf-2 protein, Dickkopf-related protein
      (DKK2), cysteine-rich secreted protein 2 (CRSP2, CRISPY2, CRSP2
      protein)
<220> FEATURE:
<221> NAME/KEY: SIGNAL
<222> LOCATION: (1)...(33)
<223> OTHER INFORMATION: signal peptide
<220> FEATURE:
<221> NAME/KEY: DOMAIN
<222> LOCATION: (77)...(129)
<223> OTHER INFORMATION: N-terminal cysteine-rich region
<220> FEATURE:
<221> NAME/KEY: DOMAIN
<222> LOCATION: (78)...(127)
<223> OTHER INFORMATION: DKK-type Cys-1 region
<220> FEATURE:
<221> NAME/KEY: DOMAIN
<222> LOCATION: (183)...(259)
<223> OTHER INFORMATION: DKK-type Cys-2 region

<400> SEQUENCE: 1

Met Ala Ala Leu Met Arg Ser Lys Asp Ser Ser Cys Cys Leu Leu Leu
            -30                 -25                 -20

Leu Ala Ala Val Leu Met Val Glu Ser Ser Gln Ile Gly Ser Ser Arg
        -15                 -10                  -5

Ala Lys Leu Asn Ser Ile Lys Ser Ser Leu Gly Gly Glu Thr Pro Gly
  1               5                  10                  15

Gln Ala Ala Asn Arg Ser Ala Gly Met Tyr Gln Gly Leu Ala Phe Gly
                 20                  25                  30

Gly Ser Lys Lys Gly Lys Asn Leu Gly Gln Ala Tyr Pro Cys Ser Ser
             35                  40                  45

Asp Lys Glu Cys Glu Val Gly Arg Tyr Cys His Ser Pro His Gln Gly
         50                  55                  60

Ser Ser Ala Cys Met Val Cys Arg Arg Lys Lys Lys Arg Cys His Arg
     65                  70                  75

Asp Gly Met Cys Cys Pro Ser Thr Arg Cys Asn Asn Gly Ile Cys Ile
 80                  85                  90                  95

Pro Val Thr Glu Ser Ile Leu Thr Pro His Ile Pro Ala Leu Asp Gly
                100                 105                 110

Thr Arg His Arg Asp Arg Asn His Gly His Tyr Ser Asn His Asp Leu
            115                 120                 125

Gly Trp Gln Asn Leu Gly Arg Pro His Thr Lys Met Ser His Ile Lys
        130                 135                 140

Gly His Glu Gly Asp Pro Cys Leu Arg Ser Ser Asp Cys Ile Glu Gly
    145                 150                 155

Phe Cys Cys Ala Arg His Phe Trp Thr Lys Ile Cys Lys Pro Val Leu
160                 165                 170                 175

His Gln Gly Glu Val Cys Thr Lys Gln Arg Lys Lys Gly Ser His Gly
                180                 185                 190

Leu Glu Ile Phe Gln Arg Cys Asp Cys Ala Lys Gly Leu Ser Cys Lys
            195                 200                 205

Val Trp Lys Asp Ala Thr Tyr Ser Ser Lys Ala Arg Leu His Val Cys
        210                 215                 220

Gln Lys Ile
        225

<210> SEQ ID NO 2
<211> LENGTH: 3659
<212> TYPE: DNA
```

```
<213> ORGANISM: Homo sapiens
<220> FEATURE:
<223> OTHER INFORMATION: Dickkopf-2 protein, Dickkopf-related protein
      (DKK2), cysteine-rich secreted protein 2 (CRSP2, CRISPY2, CRSP2
      protein)
<220> FEATURE:
<221> NAME/KEY: CDS
<222> LOCATION: (76)..(1485)
<223> OTHER INFORMATION: DKK2

<400> SEQUENCE: 2
```

| | | | | | |
|---|---|---|---|---|---|
| cgggagcccg | cggcgagcgt | agcgcaagtc | cgctccctag | gcatcgctgc | gctggcagcg | 60 |
| attcgctgtc | tcttgtgagt | caggggacaa | cgcttcgggg | caactgtgag | tgcgcgtgtg | 120 |
| ggggacctcg | attctcttca | gatctcgagg | attcggtccg | gggacgtctc | ctgatcccct | 180 |
| actaaagcgc | ctgctaactt | tgaaaaggag | cactgtgtcc | tgcaaagttt | gacacataaa | 240 |
| ggataggaaa | agagaggaga | gaaaagcaac | tgagttgaag | gagaaggagc | tgatgcgggc | 300 |
| ctcctgatca | attaagagga | gagttaaacc | gccgagatcc | cggcgggacc | aaggaggtgc | 360 |
| ggggcaagaa | ggaacggaag | cggtgcgatc | cacagggctg | ggttttcttg | caccttgggt | 420 |
| cacgcctcct | tggcgagaaa | gcgcctcgca | tttgattgct | tccagttatt | gcagaacttc | 480 |
| ctgtcctggt | ggagaagcgg | gtctcgcttg | ggttccgcta | atttctgtcc | tgaggcgtga | 540 |
| gactgagttc | atagggtcct | gggtccccga | accaggaagg | gttgagggaa | cacaatctgc | 600 |
| aagcccccgc | gacccaagtg | aggggccccg | tgttggggtc | ctccctccct | ttgcattccc | 660 |
| acccctccgg | gctttgcgtc | ttcctgggga | ccccctcgcc | gggagatggc | cgcgttgatg | 720 |
| cggagcaagg | attcgtcctg | ctgcctgctc | ctactggccg | cggtgctgat | ggtggagagc | 780 |
| tcacagatcg | gcagttcgcg | ggccaaactc | aactccatca | agtcctctct | gggcggggag | 840 |
| acgcctggtc | aggccgccaa | tcgatctgcg | ggcatgtacc | aaggactggc | attcggcggc | 900 |
| agtaagaagg | gcaaaaacct | ggggcaggcc | tacccttgta | gcagtgataa | ggagtgtgaa | 960 |
| gttgggaggt | attgccacag | tccccaccaa | ggatcatcgg | cctgcatggt | gtgtcggaga | 1020 |
| aaaaagaagc | gctgccaccg | agatggcatg | tgctgcccca | gtacccgctg | caataatggc | 1080 |
| atctgtatcc | cagttactga | aagcatctta | accoctcaca | tcccggctct | ggatggtact | 1140 |
| cggcacagag | atcgaaacca | cggtcattac | tcaaaccatg | acttgggatg | cagaatcta | 1200 |
| ggaagaccac | acactaagat | gtcacatata | aagggcatg | aaggagaccc | ctgcctacga | 1260 |
| tcatcagact | gcattgaagg | ttttgctgt | gctcgtcatt | tctggaccaa | aatctgcaaa | 1320 |
| ccagtgctcc | atcaggggga | agtctgtacc | aaacaacgca | agaagggttc | tcatgggctg | 1380 |
| gaaattttcc | agcgttgcga | ctgtgcgaag | ggcctgtctt | gcaaagtatg | aaagatgcc | 1440 |
| acctactcct | ccaaagccag | actccatgtg | tgtcagaaaa | tttgatcacc | attgaggaac | 1500 |
| atcatcaatt | gcagactgtg | aagttgtgta | tttaatgcat | tatagcatgg | tggaaaataa | 1560 |
| ggttcagatg | cagaagaatg | gctaaaataa | gaaacgtgat | aagaatatag | atgatcacaa | 1620 |
| aaagggagaa | agaaaacatg | aactgaatag | attagaatgg | gtgacaaatg | cagtgcagcc | 1680 |
| agtgttttcca | ttatgcaact | tgtctatgta | aataatgtac | acatttgtgg | aaaatgctat | 1740 |
| tattaagaga | acaagcacac | agtggaaatt | actgatgagt | agcatgtgac | tttccaagag | 1800 |
| tttaggttgt | gctggaggag | aggtttcctt | cagattgctg | attgcttata | caaataacct | 1860 |
| acatgccaga | tttctattca | acgttagagt | ttaacaaaat | actcctagaa | taacttgtta | 1920 |
| tacaataggt | tctaaaaata | aaattgctaa | acaagaaatg | aaaacatgga | gcattgttaa | 1980 |
| tttacaacag | aaaattaccct | tttgatttgt | aacactactt | ctgctgttca | atcaagagtc | 2040 |

```
ttggtagata agaaaaaaat cagtcaatat ttccaaataa ttgcaaaata atggccagtt    2100
gtttaggaag gcctttagga agacaaataa ataacaaaca aacagccaca aatacttttt    2160
tttcaaaatt ttagttttac ctgtaattaa taagaactga tacaagacaa aaacagttcc    2220
ttcagattct acggaatgac agtatatctc tctttatcct atgtgattcc tgctctgaat    2280
gcattatatt ttccaaacta tacccataaa ttgtgactag taaaatactt acacagagca    2340
gaattttcac agatggcaaa aaatttaaa gatgtccaat atatgtggga aaagagctaa     2400
cagagagatc attatttctt aaagattggc cataacctgt attttgatag aattagattg    2460
gtaaatacat gtattcatac atactctgtg gtaatagaga cttgagctgg atctgtactg    2520
cactggagta agcaagaaaa ttgggaaaac ttttttcgttt gttcaggttt tggcaacaca   2580
tagatcatat gtctgaggca caagttggct gttcatcttt gaaaccaggg gatgcacagt    2640
ctaaatgaat atctgcatgg gatttgctat cataatattt actatgcaga tgaattcagt    2700
gtgaggtcct gtgtccgtac tatcctcaaa ttatttattt tatagtgctg agatcctcaa    2760
ataatctcaa tttcaggagg tttcacaaaa tggactcctg aagtagacag agtagtgagg    2820
tttcattgcc ctctataagc ttctgactag ccaatggcat catccaattt tcttcccaaa    2880
cctctgcagc atctgcttta ttgccaaagg gctagtttcg gttttctgca gccattgcgg    2940
ttaaaaaata taagtaggat aacttgtaaa acctgcatat tgctaatcta tagacaccac    3000
agtttctaaa ttcttttgaaa ccactttact acttttttta aacttaactc agttctaaat    3060
actttgtctg gagcacaaaa caataaaagg ttatcttata gtcgtgactt taaactttg     3120 tagaccacaa ttcactttttt agtttttcttt tacttaaatc ccatctgcag tctcaaattt   3180
aagttctccc agtagagatt gagtttgagc ctgtatatct attaaaaatt tcaacttccc    3240
acatatattt actaagatga ttaagactta cattttctgc acaggtctgc aaaaacaaaa    3300
attataaact agtccatcca agaaccaaag tttgtataaa caggttgcta taagcttggt    3360
gaaatgaaaa tggaacattt caatcaaaca tttcctatat aacaattatt atatttacaa    3420 tttggttttct gcaatatttt tcttatgtcc accctttaa aaattattat ttgaagtaat    3480
ttatttacag gaaatgttaa tgagatgtat tttcttatag agatatttct tacagaaagc    3540
tttgtagcag aatatatttg cagctattga cttttgtaatt taggaaaaat gtaataaag    3600 ataaaatcta ttaattttt ctcctctaaa aactgaaaaa aaaaaaaaaa aaaaaaaa      3659
```

<210> SEQ ID NO 3
<211> LENGTH: 20
<212> TYPE: DNA
<213> ORGANISM: Artificial Sequence
<220> FEATURE:
<223> OTHER INFORMATION: synthetic DKK2 cDNA-specific primer set A, mDKK2_A primer

<400> SEQUENCE: 3
cagagatggg atgtgttgcc                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic DKK2 cDNA-specific primer set A, mDKK2_A primer

<400> SEQUENCE: 4

-continued

```
cctgatggag cactggtttg                                              20

<210> SEQ ID NO 5
<211> LENGTH: 20
<212> TYPE: DNA
<213> ORGANISM: Artificial Sequence
<220> FEATURE:
<223> OTHER INFORMATION: synthetic Tg-specific primer set B, mDKK2_B
      primer

<400> SEQUENCE: 5
gatgggtttt gttgtgctcg                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic Tg-specific primer set B, mDKK2_B
      primer

<400> SEQUENCE: 6
atgtttcagg ttcaggggga                                              20

<210> SEQ ID NO 7
<211> LENGTH: 6
<212> TYPE: PRT
<213> ORGANISM: Artificial Sequence
<220> FEATURE:
<223> OTHER INFORMATION: synthetic His-6 sequence fusion partner
      suitable for isolation

<400> SEQUENCE: 7

His His His His His His
1               5
```

COMPOSITION FOR TREATMENT OR PREVENTION OF ERECTILE DYSFUNCTION INCLUDING DKK2 PROTEIN OR DKK2 GENE THEREOF AND USE OF THE COMPOSITION

CROSS-REFERENCE TO RELATED PATENT APPLICATION

This application is the U.S. National Stage Entry under §371 of International Application No. PCT/KR2012/002734, filed Apr. 10, 2012, which claims the benefit of Korean Patent Application No. 10-2011-0083560, filed on Aug. 22, 2011, and Korean Patent Application No. 10-2012-0026614, filed on Mar. 15, 2012, in the Korean Intellectual Property Office, the disclosures of which are incorporated herein in their entirety by reference

REFERENCE TO A "SEQUENCE LISTING," A TABLE, OR A COMPUTER PROGRAM LISTING APPENDIX SUBMITTED AS AN ASCII TEXT FILE

The Sequence Listing written in file 96275-897273.TXT, created on Jan. 16, 2014, 8,192 bytes, machine format IBM-PC, MS-Windows operating system, is hereby incorporated by reference in its entirety for all purposes.

TECHNICAL FIELD

1. Field of the Invention

One or more embodiments of the present invention relate to a pharmaceutical composition for regenerating endothelial cells, a pharmaceutical composition for treatment or prevention of erectile dysfunction, a method of regenerating an endothelial cell of a subject, and a method of preventing or treating erectile dysfunction in a subject.

2. Background Art

DKK2, which is a member of the Dickkopf family and a repressor protein of Wnt protein, has been reported to act as an inhibiting factor or stimulating factor of signaling pathways of Wnt (Wu W et. al., Curr. Biol., 10(24), pp. 1611-1614, 2000). It has two specific cysteine-rich domains (CRDs) and is divided into various lengths of connection regions. In particular, a protein belonging to the Dickkopf family has highly conserved a cystein-2 region with 10 conserved cysteine residues between the family members (Krupnik V E et al., Gene, 238(2), pp. 301-313, 1999). It has been reported that DKK2 is closely correlated with osteoclast differentiation (Li X et al., Nat. Genet., 37(9), pp. 945-952, 2005). However, there is no report or disclosure about the effect of DKK2 on the prevention or treatment of erectile dysfunction.

Erectile dysfunction is a male sexual dysfunction characterized by the inability to develop or maintain an erection of the penis during sexual intercourse. There are two major causes for erectile dysfunction: psychogenic and organic causes. The psychogenic cause is attributed to the activation of sympathetic nervous system and inhibition of nonadrenergic-noncholinergic nerve system by psychological or mental effect, which elicits an increase in the smooth muscle tension of corpus cavernosum (erectile tissue of the penis) and resultant erectile dysfunction. The organic erectile dysfunctions are divided into neurogenic, vasculogenic, and endocrine erectile dysfunctions according to the cause.

The vasculogenic erectile dysfunction is known to cause insufficient secretion of relaxation neurotransmitters (e.g., nitric oxide (NO)) from cavernous endothelial cells due to endothelial dysfunction that are caused by hyperlipidemia, diabetes mellitus, high blood pressure, smoking, metabolic syndrome, other vascular risk factors, etc.

Recent researches associated with erectile dysfunction have intensely focused on the organic erectile dysfunction. And phosphodiesterase-5 (PDE-5) inhibitors for oral administration including Viagra (Sildenafil s trade name) are widely utilized as first-line therapy for erectile dysfunction. Oral PDE-5 inhibitors are well known to be effective for the treatment of erectile dysfunction by potentiating the physiologic erectile response to NO and by amplifying the NO-cyclicGMP pathway through competitive inhibition of cyclic GMP degradation.

However, more than 30% of total patients with erectile dysfunction, including diabetic patients, those with spinal cord injuries and those who underwent radical prostatectomy for the treatment for prostatic cancer, etc, do not respond to oral PDE-5 inhibitors. Moreover, adverse events associated with PDE-5 inhibitor treatment such as headache, facial flushing, indigestion, back pain/myalgia, visual disturbance are not infrequent. In addition, these treatments have also some restrictions in their application. PDE-5 inhibitors are absolutely contraindicated for patients using nitrates and are either not recommended or to be used with caution in men with severe cardiovascular disease such as unstable angina, cardiac failure, recent myocardial infarct, poorly controlled blood pressure, in men who takes ketokonazole, itraconazole, ritonavir, alpha-adrenergic blocker, and in patients with severe hepatic insufficiency or renal insufficiency, etc. Furthermore, PDE5 inhibitors are used as on demand medicines but not effective to cure underlying disease at all, which limits the spontaneity of the sexual activity and causes higher drop out rate of the treatment.

DISCLOSURE OF INVENTION

Technical Problem

Therefore, new therapeutic strategies are needed for erectile dysfunction, which allows long-lasting treatment effect through the restoration of healthy erectile tissue, including the regeneration of cavernous endothelium.

Solution to Problem

The present invention provides a pharmaceutical composition for regenerating endothelial cells.

The present invention also provides a pharmaceutical composition for preventing or treating erectile dysfunction.

The present invention also provides a method of regenerating endothelial cells of a subject.

The present invention also provides a method of preventing or treating erectile dysfunction of a subject.

Advantageous Effects of Invention

As described above, according to the one or more embodiments of the present invention, by using a pharmaceutical composition for regenerating endothelial cells, damaged endothelial cells of a subject may be regenerated. In addition, a pharmaceutical composition for preventing or treating erectile dysfunction may be utilized for the prevention or treatment of erectile dysfunction of a subject. According to the method of regenerating endothelial cells of a subject, damaged endothelial cells of a subject may be regenerated. In addition, according to a method of preventing or treating erectile dysfunction of a subject, erectile dysfunction may be prevented or treated. In addition, erectile dysfunction may be treated and prevented in subjects who have vascular diseases by the method according to the present invention.

BRIEF DESCRIPTION OF DRAWINGS

The above and other features and advantages of the present invention will become more apparent by describing in detail exemplary embodiments thereof with reference to the attached drawings in which.

BEST MODE FOR CARRYING OUT THE INVENTION

One or more embodiments of the present invention will now be described more fully with reference to the following examples. These examples are provided only for illustrative purposes and are not intended to limit the scope of the invention.

Example 1

Effect of DKK2 Gene Treatment on Erectile Function in Hyperlipidemia-Induced Erectile Dysfunction Model Two-month-old male C57BL/6J mice were fed a normal diet for 3 months as a control, and two-month-old male C57BL/6J mice were fed a high cholesterol diet (4% cholesterol+1% cholic acid) for 3 months as an experimental group. As the normal diet, a general feed not including a high cholesterol diet (consisting of about 20% or more of protein, about 5% or more of lipid, extra vitamins and minerals) was orally administered to the mice everyday as required (a daily feed amount was not fixed and the mice were fed sufficiently). As the high cholesterol diet, a normal diet supplemented with 4% cholesterol +1% cholic acid was orally administered to the mice by using the same method as that used for the normal diet. The mice were fed a high cholesterol diet for 3 months to have high cholesterol diet-induced erectile dysfunction.

For the experiment, the mice were divided into 7 groups (N=4-7 mice/group; $1^{st}$ group: normal control group; $2^{nd}$ group: high cholesterol diet group; $3^{rd}$ group: high cholesterol diet group+virus vehicle [$2\times10^8$ particles/20 μL]; $4^{th}$ group: high cholesterol diet group+adenovirus encoding DKK2 gene [ad-DKK2, $1\times10^8$ particles/20 μL]; $5^{th}$ group: high cholesterol diet group+ad-DKK2 [$2\times10^8$ particles/20 μL]; $6^{th}$ group: high cholesterol diet group+ad-DKK2 [$1\times10^9$ particles/20 μL]; and $7^{th}$ group: high cholesterol diet group+ad-DKK2 [$2\times10^9$ particles/20 μL]). In this regard, the virus vehicle refers to a virus vehicle into which a DKK2 gene is not introduced, i.e., adenovirus particles.

Evaluation of erectile function in response to electrical stimulation of cavernous nerve goes as follows. Two weeks after intracavernous injection of DKK2 gene or empty virus vehicle, erectile function in response to cavernous nerve stimulation was evaluated by measurement of intracavernous pressure and systemic blood pressure. Each animal was anesthetized and the penis was exposed. Bipolar platinum wire electrodes were placed around the cavernous nerve. Stimulation parameters were 1-5 V at a frequency of 12 Hz, a pulse width of 1 ms, and a duration of 1 min. During tumescence, the maximal intracavernous pressure (ICP) was recorded. The total ICP was determined by the area under the curve from the beginning of cavernous nerve stimulation to a point 20 s after termination of the stimulus. Systemic blood pressure was measured by using a noninvasive tail-cuff system. The ratios of maximal ICP and total ICP (area under the curve) to mean systolic blood pressure (MSBP) were calculated to adjust for variations in systemic blood pressure.

Figure 1:
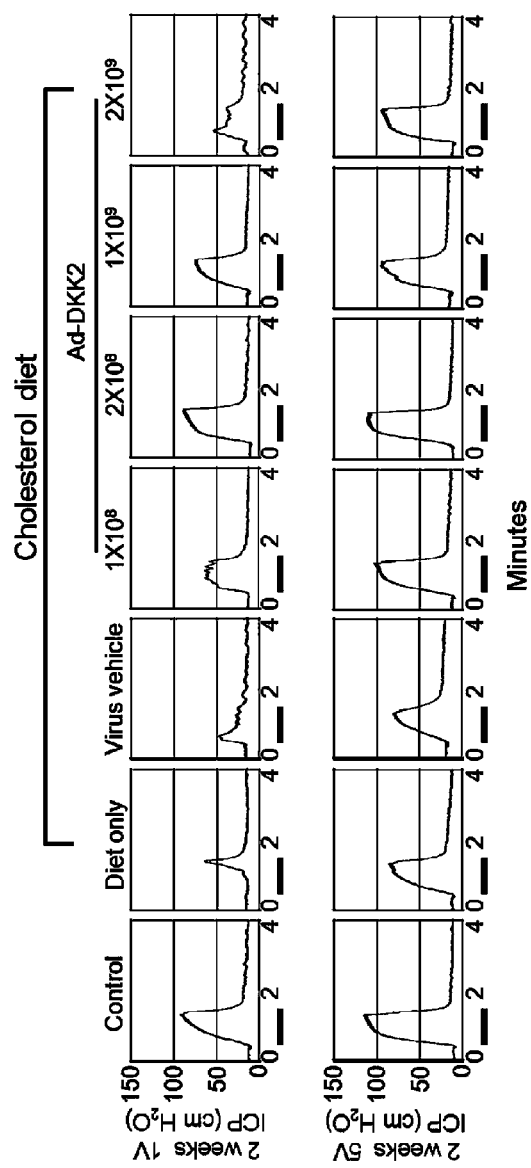
FIGS. 1, 2, and 3 are graphs showing erectile response (ICP=intracavernous pressure, MaxICP/MSBP=Maximal Intracavernous Pressue/Mean Systemic Blood Pressure, Total ICP/MSBP=Area Under Curve) to electrical stimulation of cavernous nerve (stimulation parameters; 1 and 5 V at a frequency of 12 Hz, a pulse width of 1 ms, and a duration of 1 minute) in a high cholesterol diet mouse group administered with a DKK2 gene or a control, according to embodiments of the present invention.
Figure 2:
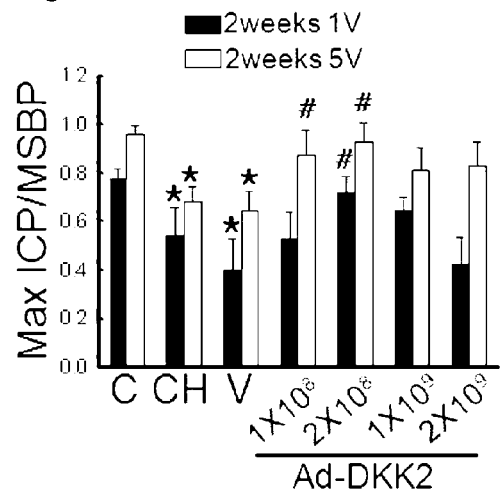
Figure 3:
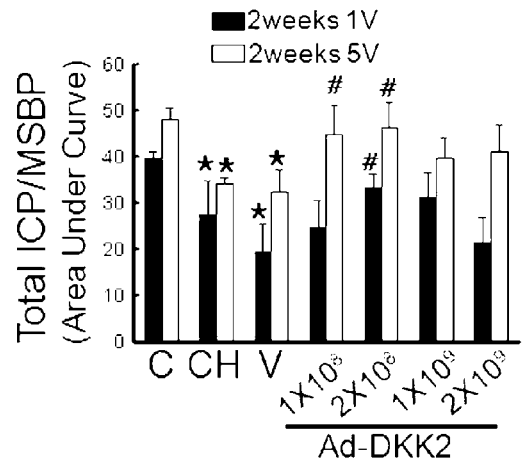

As results, FIG. 1 shows representative tracing of ICP in response to electrical stimulation of cavernous nerves in the control group and high cholesterol diet groups treated with either DKK2 gene or vehicle only or without any treatment. FIG. 2 and FIG. 3 show Maximal ICP/MSBP and Total ICP/MSBP, which are utilized for erection indices, were statistically analyzed in those groups.

As illustrated in FIGS. 1, 2, and 3, cholesterol groups treated with Ad-DKK2 exhibited greater restoration of erectile function in terms of maximal ICP/MSBP and Total ICP/MSBP than that cholesterol diet only group or the group treated with virus vehicle. Of the cholesterol groups treated with Ad-DKK2, the group with a concentration of $2\times10^8$ exhibited the highest improvement effect on erectile function, which almost reached that of normal control group. In FIGS. 2 and 3, C refers to control group, CH refers to cholesterol diet only group, and V refers to virus vehicle group.

Therefore, DKK2 gene therapy by present invention markedly restored penile erection in hypercholesterolemia-induced erectile dysfunction.

Evaluation of Expressions of Endothelial Cell-Specific Protein, PECAM-1, and Activity of p-eNOS The penis is a kind of special vascular organ. For normal penile erection, the endothelium from the corpora cavernosa (erectile tissue) and penile blood vessels should be intact both structurally and functionally. In particular, an endothelial nitric oxide synthase (eNOS) produced from cavernous endothelial cells is a major enzyme that produces a nitric oxide (NO) that plays a crucial role in relaxation of corpora cavernosa and penile blood vessels and resultant penile erection. Any abnormailty in endothelial function or structure (endothelial dysfunction) inevitably results in erectile dysfunction.

Therefore, immunohistochemical staining for platelet/endothelial cell adhesion molucule-1 (PECAM-1) and phosphorylated endothelial nitric oxide synthase (p-eNOS) from the hypercholesterolemic mice were performed to evaluate whether and how intracavernous treatment of DKK2 gene has an effect to regenerate cavernous endothelium as one of the mechanisms responsible for the restoration of penile erection, described above.

Cavernous expression of a vascular endothelial cell and the amount of p-eNOS in cholesterol diet group without treatment or that treated with vehicle only were significantly decreased as compared to those of the normal control group. In contrast, cavernous expression of p-eNOS was restored to nearly a normal level in cholesterol diet group treated with DKK2 gene.

Mice were fed corresponding diets of the $1^{st}$, $2^{nd}$, $3^{rd}$, and $5^{th}$ groups, respectively, for 3 months, thereby inducing hyperlipidemia. A penile tissue of each group was fixed in 4% formaldehyde at 4° C. for 24 hours and then cut to a thickness of 8 μm in a cryostat microtome, thereby preparing a penile tissue section.

Next, the penile tissue section was mounted on a slide, and fixed in 3.7% paraformaldehyde for about 5 minutes in order to analyze the expression of PECAM-1 and the activity of p-eNOS. The fixed penile tissue sections were washed three times with a washing buffer (2% FBS+0.1% sodium azide in PBS) and then reacted with a first antibody (i.e., hamster anti-PECAM-1 antibody and rabbit anti-p-eNOS antibody) at a ratio of 1:100 at 4° C. for 16 hours. Then, to remove the remaining antibodies, the resultant penile tissue sections were washed three times with a washing buffer, and then reacted with a second antibody (FITC-labeled anti-rabbit antibody and TRITC-labeled anti-hamster antibody), which was designed to confirm antibodies specifically reactive to PECAM-1 and p-eNOS by fluorescence, at a ratio of 1:1000 at room temperature for 1 hour. And then, to remove the remnant antibodies, each penile tissue section was washed again three times with a washing buffer. Then, expression pattern of PECAM-1 and p-eNOS were analyzed using a fluorescent microscope or a confocal microscope to trace fluorescent materials.

Figure 4:
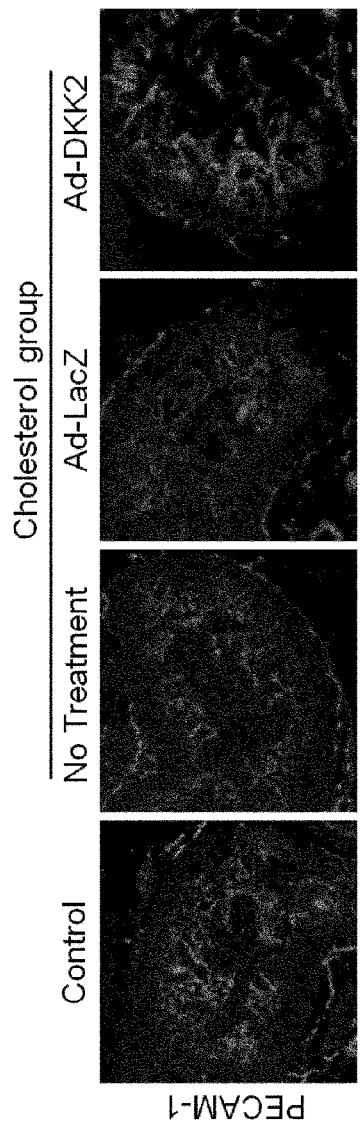
FIG. 4 illustrates confocal microscopic images showing expression pattern of PECAM-1 in penile tissues of a high cholesterol diet mouse group administered with a DKK2 gene and a control, according to an embodiment of the present invention.
Figure 5:
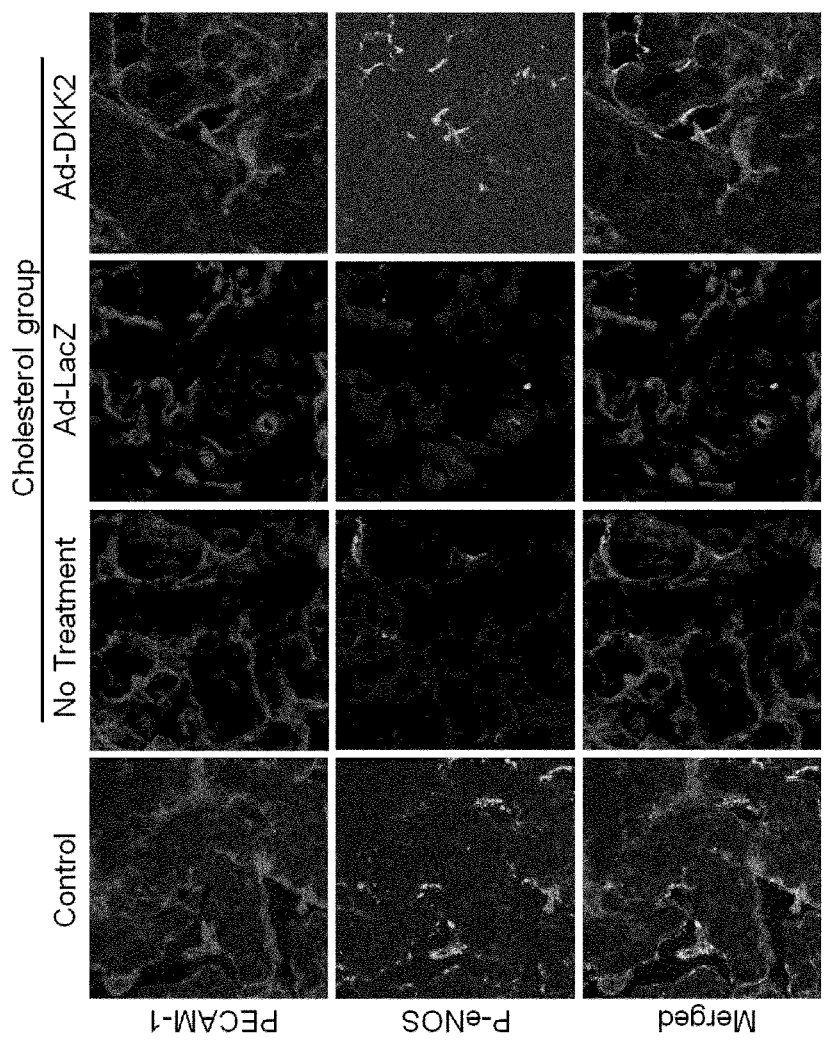
FIG. 5 illustrates confocal microscopic images showing expression pattern of PECAM-1 and phosphorylated endothelial NO synthase (p-eNOS) in penile tissues of a high cholesterol diet mouse group administered with a DKK2 gene and a control, according to an embodiment of the present invention.

And the results are shown in FIGS. 4 and 5. FIG. 4 illustrates confocal microscopic images showing expression pattern of PECAM-1 in penile tissues of the cholesterol diet group administered with DKK2 and the control. As shown in FIG. 4, the number of cavernous endothelial cells significantly decreased in penises of the cholesterol groups, as compared to the control. In FIG. 4, the image of control denotes results for a penile tissue section prepared using the same method as that used to prepare the experimental groups, except that the mice were fed a diet corresponding to the $1^{st}$ group. An expression level of the endothelial cell-specific protein increased in the group treated with Ad-DKK2, as compared with the group without any treatment or that treated with Ad-LacZ. This indicates that treatment of DKK2 gene promoted regeneration of cavernous endothelial cells from the hypercholesterolemic mice, which in turn resulted in restoration of erectile function.

FIG. 5 illustrates confocal microscopic images showing expression pattern of PECAM-1 and p-eNOS in penile tissues of a cholesterol group treated with Ad-DKK2 and a control. Cavernous expression of p-eNOS in cholesterol diet group without treatment or that treated with vehicle only were significantly decreased as compared to those of the normal control group. In contrast, cavernous expression of p-eNOS was restored to nearly a normal level in cholesterol diet group treated with DKK2 gene.

This indicates that treatment of DKK2 gene enhanced cavernous eNOS activity up to normal level in the hypercholesterolemic mice, which is responsible for restoration of erectile function.

Example 2

Overexpression of DKK2 Gene and Treatment Effect of DKK2 Protein on Erectile Dysfunction in Diabetes-Induced Erectile Dysfunction Model (1) Effect of DKK2 Gene Overexpression on Preservation of Erectile Function in Diabetes-Induced Erectile Dysfunction Model To more accurately verify a function of a DKK2 gene in diabetes-induced erectile dysfunction, a study using a DKK2 overexpression mouse (DKK2 transgenic mouse) was conducted. A DKK2 transgenic mouse, a transgenic Tg mouse that expresses mouse DKK2 (mDKK2) was designed using endothelial cell (EC)-specific Tie2 promoter/enhancer (refer to FIGS. 6A, 6B, 6C, and 6D).

Figure 6:
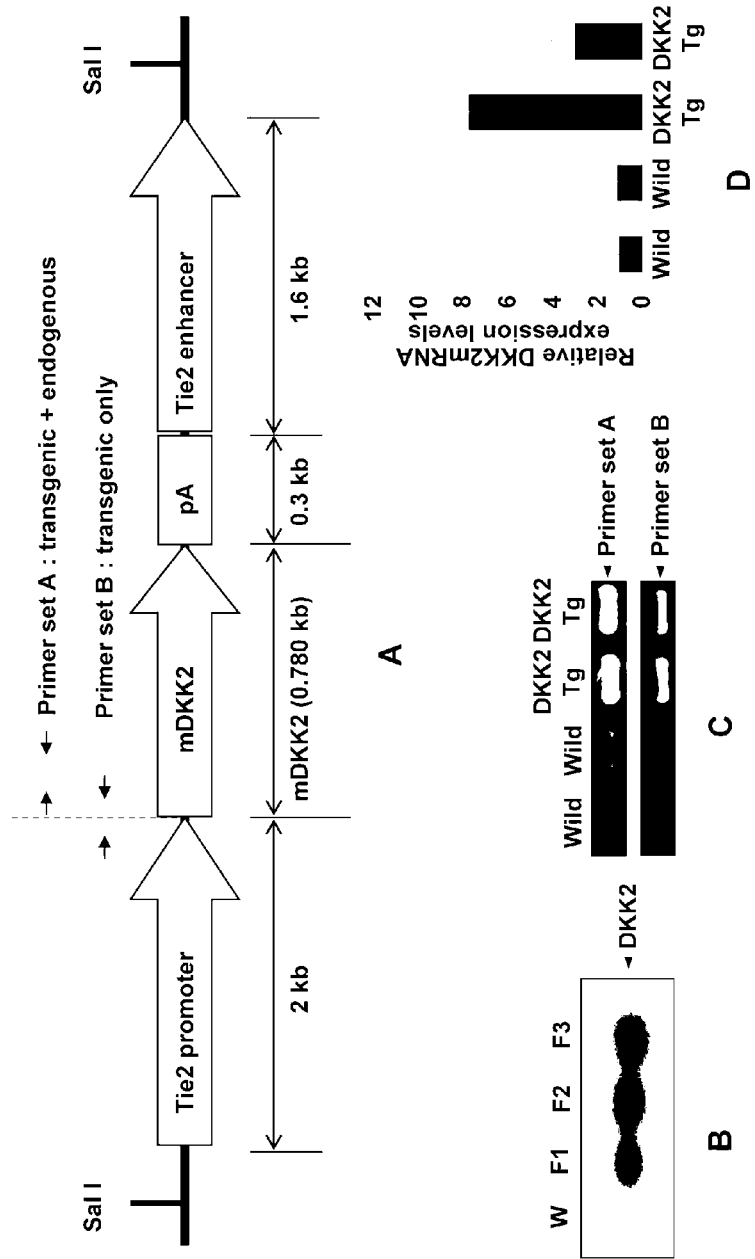
FIGS. 6A, 6B, 6C, and 6D are views illustrating analysis results of gene constructs used to obtain EC-specific DKK2 transgenic (Tg) mice and the obtained EC-specific DKK2 Tg mice, according to embodiments of the present invention.

FIG. 6A is a view illustrating a gene construct designed to allow DKK2 to be specifically expressed in endothelial cells. FIG. 6B is a photograph showing the confirmation results of the presence of transgenes in founder mice by western blotting. Three DKK2 founder mice per group were identified. FIG. 6C is an image showing RT-PCR results of total RNA extracted from P12 mouse retinas by using primer set A (DKK2 cDNA-specific primer set: SEQ ID NOS: 3 and 4) and primer set B (Tg-specific primer set: SEQ ID NOS: 5 and 6), through which confirmed Tg-specific DKK2 expression. FIG. 6D is a graph showing real-time RT-PCT results using primer set A.

In this experiment, two-month-old male C57BL/6J mice were used and divided into 4 groups (N=8 mice/group; $1^{st}$ group: wild-type mouse; $2^{nd}$ group: DKK2 transgenic mouse; $3^{rd}$ group: wild-type mouse+induction of diabetes using streptozotocin [intraperitoneal administration at a concentration of 50 mg/kg for 5 consecutive days]; $4^{th}$ group: DKK2 transgenic mouse+induction of diabetes using streptozotocin [intraperitoneal administration at a concentration of 50 mg/kg for 5 consecutive days]. Eight weeks after the induction of diabetes, every mouse was subjected to evaluate erectile function to cavernous nerve stimulation or cavernous histology, including immunohistochemical staining for PECAM-1 and p-eNOS, as described previously.

Figure 7:
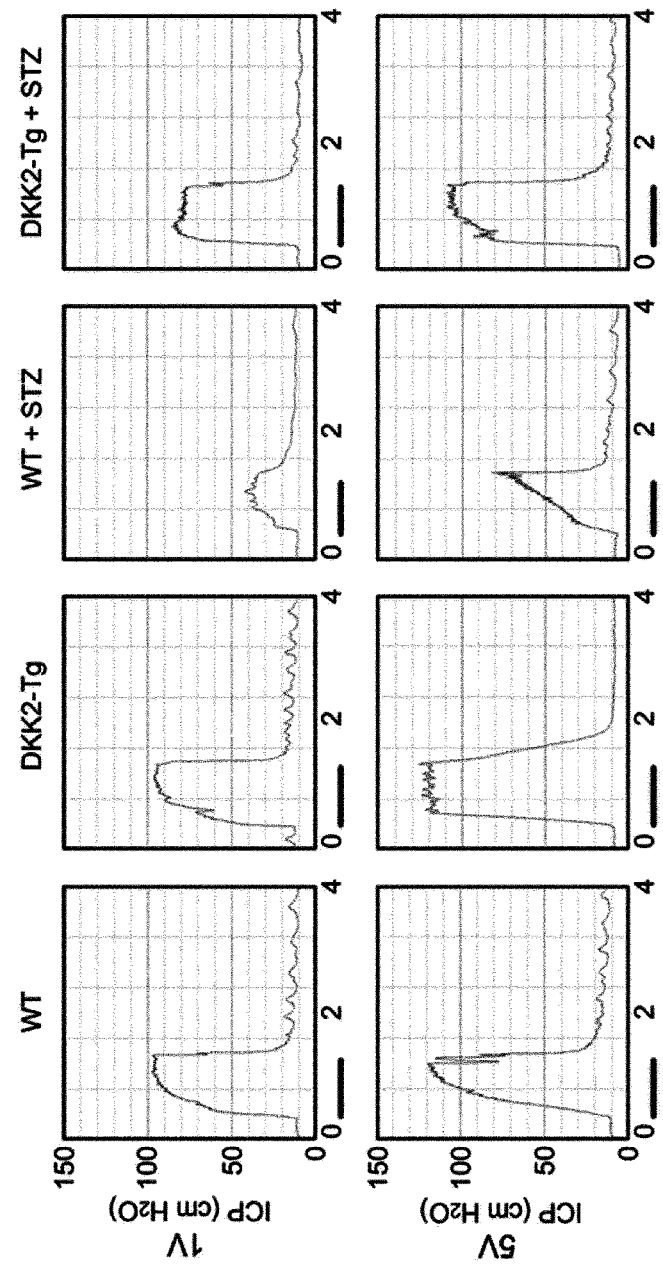
FIGS. 7, 8, and 9 are graphs showing erectile response to electrical stimulation of cavernous nerve in DKK2 transgenic or non-transgenic, diabetic or nondiabetic mouse groups, according to embodiments of the present invention.
Figure 8:
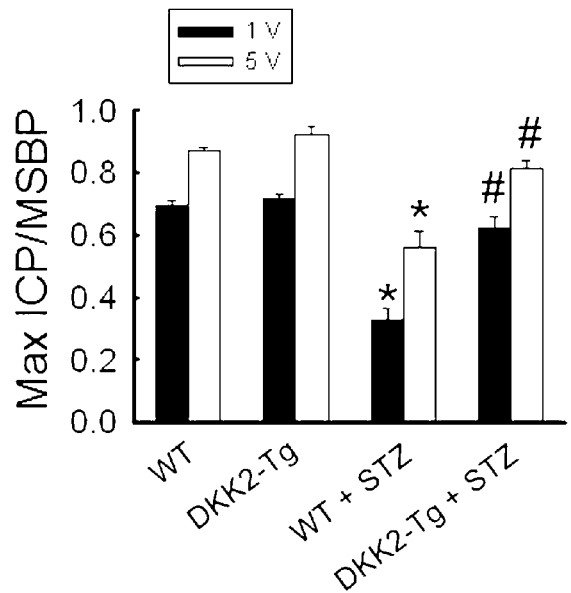
Figure 9:
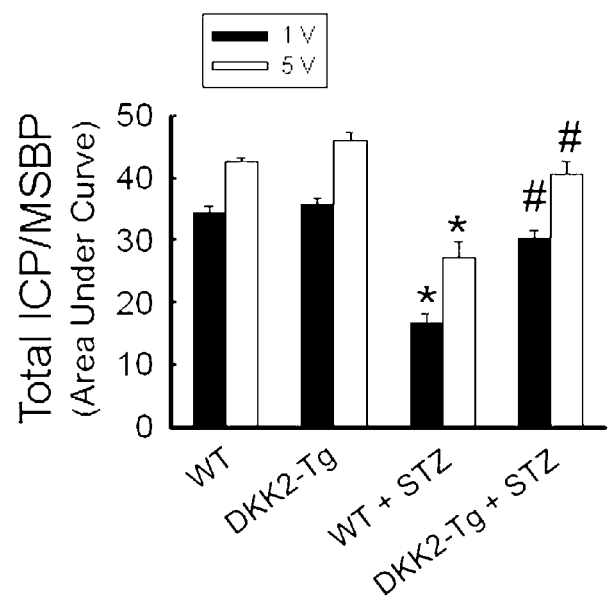

In results, FIGS. 7, 8, and 9 are illustrates showing erectile responses to electrical stimulation of cavernous nerve in DKK2 transgenic or non-transgenic, diabetic or non-diabetic mouse groups.

As shown in FIGS. 7, 8, and 9, a wild-type mouse group with diabetes exhibited significantly decreased erectile response, compared with a wild-type control group. In contrast, a DKK2 transgenic mouse group (DKK2-Tg) with diabetes showed greater preservation of erectile function, compared with a wild type diabetic mouse, which was comparable to that in the normal mouse.

Figure 10:
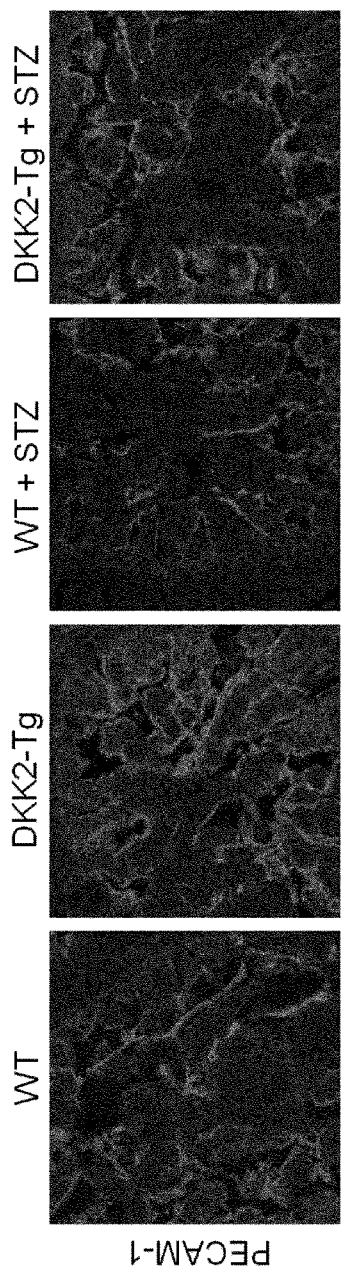
FIG. 10 illustrates confocal microscopic images showing expression pattern of PECAM-1 (endothelial cell marker protein) in penile erectile tissues of DKK2 transgenic or non-transgenic, diabetic or nondiabetic mouse groups, according to an embodiment of the present invention.

FIG. 10 illustrates confocal microscopic images showing expression pattern of PECAM-1 in erectile tissues from DKK2 transgenic or non-transgenic, diabetes or non-diabetes mouse groups. As shown in FIG. 10, cavernous endothelial cell contents significantly decreased in a wild-type mouse group with diabetes, compared with that in a wild-type control. In contrast, compared with wild type mouse group with diabetes, the DKK2 transgenic mouse group (DKK2-Tg) with diabetes showed greater preservation of cavernous endothelial contents, evidenced by more increase in PECAM-1 positive expression, which was comparable to that in the control. This indicates that overexpression of the DKK2 gene promotes the regeneration or preservation of cavernous endothelial cells, which also enhances restoration of erectile function.

Figure 11:
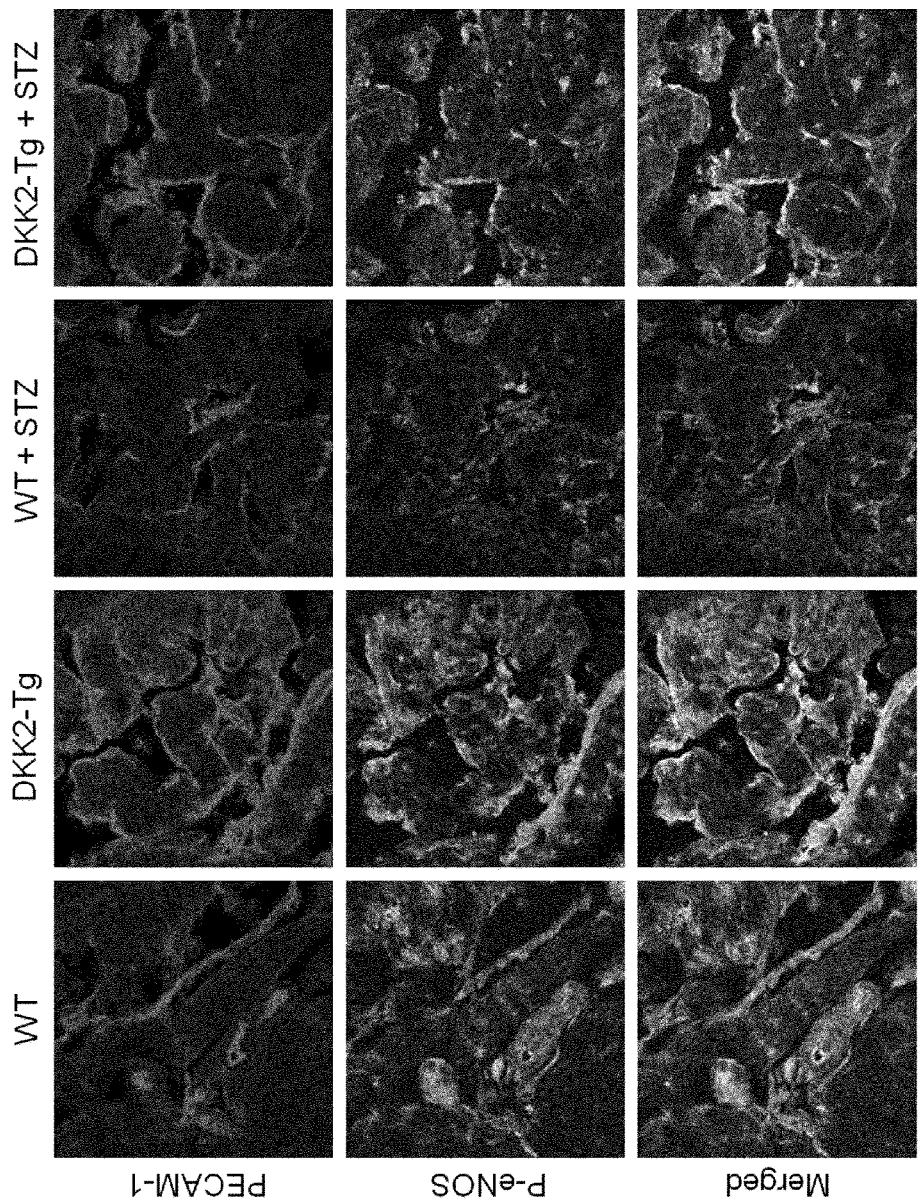
FIG. 11 illustrates confocal microscopic images showing expression pattern of PECAM-1 and p-eNOS in penile erectile tissues of DKK2 transgenic or non-transgenic, diabetic or non-diabetic mouse groups, according to an embodiment of the present invention.

FIG. 11 illustrates confocal microscopic images showing expression pattern of PECAM-1 and p-eNOS in penile erectile tissues of DKK2 transgenic or non-transgenic, diabetes or non-diabetes mouse groups. As shown in FIG. 11, a greater decrease in the expression of p-eNOS was shown in a wild-type mouse group with diabetes than in a wild-type control. In contrast, a DKK2 transgenic mouse group (DKK2-Tg) with diabetes showed a less decrease in the expression of p-eNOS compared with that in wild type mouse with diabetes. This indicates that overexpression of DKK2 promotes or preserves the eNOS activity in the diabetic condition, which enhances penile erection.

Figure 12:
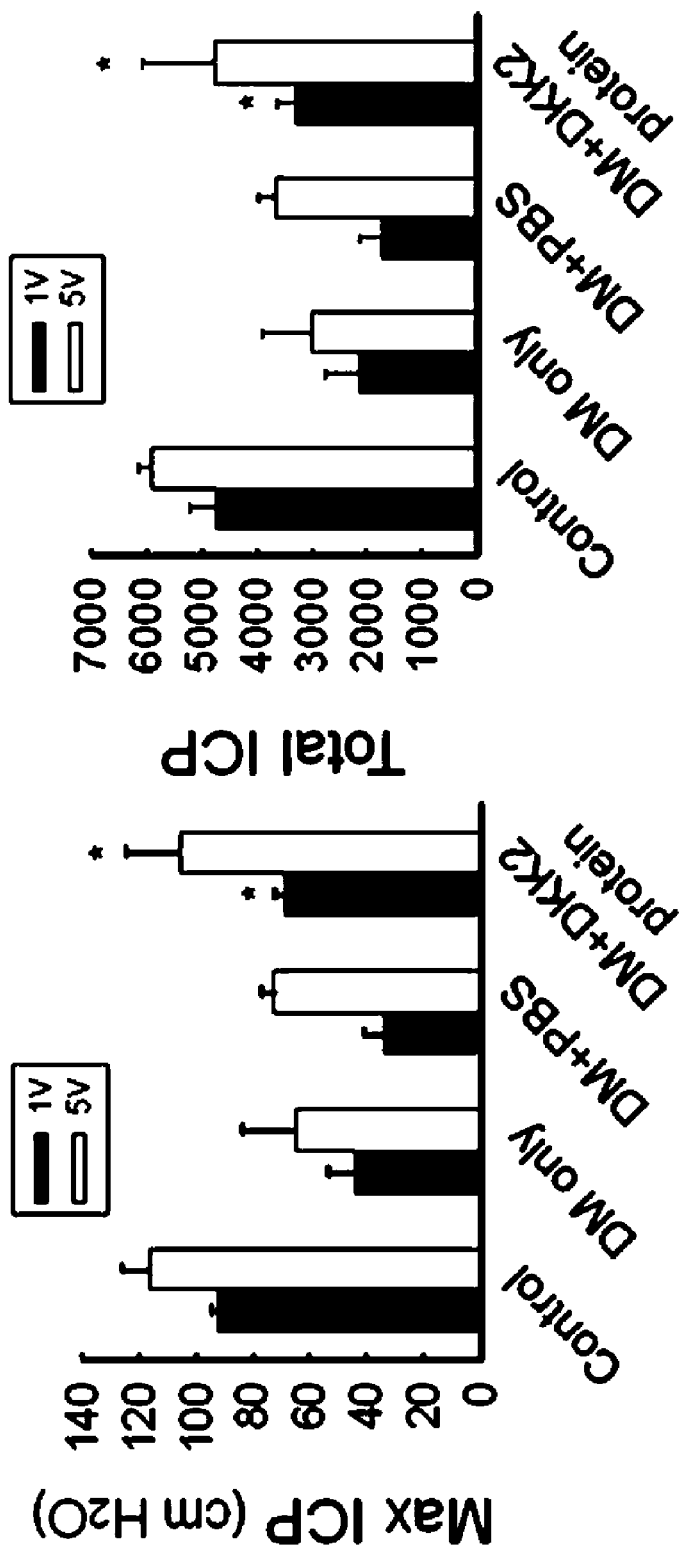
FIG. 12 illustrates graphs showing erectile response to electrical stimulation of cavernous nerve in diabetic mouse group administered with DKK2 protein and a control (normal mouse group), according to an embodiment of the present invention.

(2) Effect of DKK2 Protein on Erectile Function in the Diabetic Erectile Dysfunction Model In 2-month-old male C57BL/6J mouse diabetes mellitus was induced by intraperitoneal injection of streptozotocin, as described previously. Mice were subjected to be treated with either none, intracavernous injection of PBS or DKK2 protein 8 weeks after the induction of diabetes and were divided into 4 groups (N=6 mice/group; $1^{st}$ group: control (WT); $2^{nd}$ group: diabetes+no treatment; $3^{rd}$ group: diabetes+phosphate buffered solution (PBS); $4^{th}$ group: diabetes+6 μg of DKK2 protein). The DKK2 protein was administered in the form of 20 μL of PBS solution. Erectile function in each mouse was evaluated 2 weeks after the intracavernous injection of either PBS or DKK2 protein. In results, FIG. 12 shows erectile responses to electrical stimulation of cavernous nerve in a diabetic mouse group either treated with DKK2 protein or a control (wild-type mouse group). Each of a plurality of bars denotes average±standard deviation (SD) per group, and * denotes P<0.05 compared with DM only group or the DM+PBS group As shown in FIG. 12, the diabetic group treated with DKK2 (DM+DKK2 protein) exhibited a significant increase in two variables in penile erection, i.e., a maximal ICP (left side in FIG. 12) and a total ICP (right side in FIG. 12), compared with those in diabetic group without the treatment (DM only) or diabetic group treated with PBS (DM+PBS) (analysis of variance (ANOVA), p<0.05). This indicates that the DKK2 protein remarkably improves penile erection in diabetic erectile dysfunction.

MODE FOR THE INVENTION

Hereinafter, exemplary embodiments of the present invention will be described in detail with reference to the accompanying drawings. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a pharmaceutical composition for regenerating endothelial cells, including as an active ingredient a DKK2 protein or a polynucleotide encoding the DKK2 protein.

As used herein, the term DKK2 refers to Dickkopf-2 protein, and is also known as Dickkopf-related protein 2, cysteine-rich secreted protein 2, CRSP2, CRISPY2, or CRSP 2 protein. DKK2 is a protein, a member of the Dickkopf family, encoded by the DKK2 gene in humans. It is known that DKK2, a secreted protein, contains two cysteine-rich regions and is involved in embryonic development through its interactions with a Wnt signaling pathway. In addition, it can act as either a promoter or antagonist of Wnt/beta-catenin signaling, depending on the cellular context and the presence of a cofactor kremen 2. The present inventors have newly found that a DKK2 protein or a gene encoding the DKK2 protein has an activity of inducing the regeneration of endothelial cells. The regeneration may include promoting the growth and/or proliferation of endothelial cells. DKK2 may encompass an amino acid sequence of, for example, SEQ ID NO: 1 or a sequence with its 1-33 sequences removed. The amino acid sequence of SEQ ID NO: 1 is a sequence of human DKK2, corresponds to GenBank accession no. NP_055236, and consists of 259aa. The sequence 1-33 is a signal peptide, 77-129 is an N terminal cysteine-rich region, 78-127 and 183-259 are referred to as DKK-type Cys-1 and DKK-type Cys-2 regions, respectively. The DKK2 may be encoded by a gene having a nucleotide sequence of 706-1482 of SEQ ID NO: 2 (GenBank accession no. NM_014421).

The DKK2 protein, of which the biological or pharmacological function and the activity was found by present inventors, includes a whole DKK2 or a physiologically active fragment thereof. The physiologically active fragment(s) may substantially correspond to those who have an activity of a DKK2 protein or a gene encoding the DKK2 protein that regenerates vascular endothelial cells. The physiologically active fragment may include an active domain involved in vascular endothelial cell activity of natural DKK2. The DKK2 protein includes a DKK2 full-length protein, a physiologically active fragment thereof, a fusion protein thereof. The fusion protein may substantially have an activity of a DKK2 protein or a gene encoding the DKK2 protein that regenerates vascular endothelial cells. The fusion protein may correspond to those who have a structure in which a DKK2 protein or a fragment thereof is linked to a fusion partner suitable for isolation of the DKK2 protein or the fragment thereof, a fusion partner suitable for transduction of the DKK2 protein or the fragment thereof to a target site, or a fusion partner for increasing the stability thereof in the body. The linkage between DKK2 protein or its fragment and its fusion partner may be made via an N-terminal, a C-terminal, or a side chain of a DKK2 protein or a fragment thereof. The linkage may be made by covalent binding or non-covalent binding. The fusion partner may include a form of polypeptide. The fusion partner suitable for isolation of a DKK2 protein or a fragment thereof may include a His sequence, for example, a His$_6$ (SEQ ID NO:7) sequence. Examples of a fusion partner suitable for transduction of the DKK2 protein or the fragment thereof to a target site or a fusion partner for increasing the stability thereof in the body include antibody constant regions such as an Fc region or polymers that provide a resistance to in vivo degradation, such as PEG.

The polynucleotide encoding DKK2 may include a nucleotide sequence that encodes an amino acid sequence of SEQ ID NO: 1. The polynucleotide encoding DKK2 may also include a nucleotide sequence of 706-1482 of SEQ ID NO: 2.

For example, the other materials can be defined to be one of the materials or a part of grouped materials which enhance intracellular delivery of the polynucleotide encoding DKK-2, or one of those which facilitates intracellular expression of the polynucleotide encoding DKK-2 by a gene expression system therein, and one of those which enable the polynucleotide encoding DKK-2 to be maintained inside and/or outside of a cell in a stable manner. The fusion includes a form of covalent binding or non-covalent binding, and also includes a form of encapsulation in a vesicle.

The polynucleotide encoding DKK-2 may be one of those which are operatively linked to a gene expression regulator such as a promoter, an operator, an enhancer, and/or a transcription terminator. For example, the polynucleotide encoding DKK-2 includes a form, which is mediated by a plasmid or virus genome so as to be delivered into the cell and expressed in the cell. The polynucleotide encoding DKK-2 may be linked with a certain regulator so as to be specifically expressed in the cavernous endothelial cells or penile vascular endothelial cells. For example, the polynucleotide encoding DKK-2 can be in the form of a structure that is inserted into an Adenovirus genome and linked to a regulator so as to be specifically expressed in the cavernous endothelial cells or penile vascular endothelial cells. The structure includes that is encapsulated in virus particles.

As used herein, the term "active ingredient" includes substances having an activity that promotes regeneration of endothelial cells especially in case when the composition is administered into a subject, compared with the case when it is not administered. The subject may be a mammal, for example, at least one selected from the group consisting of a human, a mouse, a hamster, a dog, a cat, a horse, a cow, a pig, and a goat.

As used herein, the term "endothelial cell" intends to include the cavernous endothelial cell or a penile vascular endothelial cell.

The composition may include a known ingredient having an activity to regenerate endothelial cells. The composition may further include a pharmaceutically acceptable carrier. The carrier includes an adjuvant, an excipient, and/or a diluent that is known in the concerned field. Examples of the carrier include aqueous solution such as a saline solution, sterile water, a Ringer s solution, a buffer, a dextrose solution, a maltodextrin solution, glycerol, or ethanol. The composition further includes a known ingredient having an activity to regenerate an endothelial cell.

The composition may be those formulated for oral administration or parenteral administration. For example, the formulation for oral administration may imply one of those consisting of granules, powder, liquid, a tablet, a capsule, and dried syrup. For example, the formulation for parenteral administration may imply an injectable solution or a composition for external application to the skin. The composition for external application to the skin may include the form of creams, lotions, or patches.

According to another embodiment of the present invention, there is provided a pharmaceutical composition for preventing or treating erectile dysfunction, including as an active ingredient of a DKK2 protein or a polynucleotide encoding the DKK2 protein.

As used herein, the term "active ingredient" may include substances having an activity in the treatment or prevention of erectile dysfunction, especially in case when the composition is administered into a subject, compared with the case when it is not administered. The subject may include a mammal, for example, at least one selected from the group consisting of a human, a mouse, a hamster, a dog, a cat, a horse, a cow, a pig, and a goat.

The term "preventing" used herein is understood to include prevention of a decrease in erectility or a decrease in a lasting time of an erection.

The term "prevention" or "prevent" used herein implies that preventing a subject suffering from erectile dysfunction, in which either initiation or maintenance of penile erection is not appropriate. For example, if erectile dysfunction is caused by a spinal cord injury or surgery, including radical prostatectomy, which accounts for 20 to 30% of the total cases of erectile dysfunction, endothelial cell death or apoptosis is inevitable for a certain period of time right after the nerve injury. In this case, a composition according to the embodiment of the present invention may be administered to an erectile tissue at the early stage, thereby preventing erectile dysfunction or rehabilitating the erectile tissue.

The term "treatment" or "treat" used herein implies significant restoration of erectile function in the initiation or maintenance of erection, compared with when the composition is not administered.

The terms "DKK2 protein" and "polynucleotide encoding DKK2" used herein are the same as defined above.

The composition may further include a pharmaceutically acceptable carrier. The carrier may be an adjuvant, an excipient, and/or a diluent that is known in the art. Examples of the carrier include aqueous solution such as a saline solution and sterile water, a Ringer's solution, a buffer, a dextrose solution, a maltodextrin solution, glycerol, and ethanol. The composition may further include a known ingredient having an activity to regenerate an endothelial cell.

The composition may increase an intracavernous pressure (ICP). The composition may increase the level of an endothelial cell-specific protein in an endothelial cell. The endothelial cell-specific protein may be platelet/endothelial cell adhesion molecule-1 (PECAM-1). The endothelial cell may be a penile corpus cavernosum endothelial cell or a penile vascular endothelial cell.

The erectile dysfunction can be resulted from disorder of or damage to penile endothelial cell (endothelial dysfunction). Endothelial dysfunction may be caused by dyslipidemia (including hypercholesterolemia), diabetes mellitus, high blood pressure, cavernous nerve injury, or, combinations thereof.

The composition can be formulated for oral administration or parenteral administration. For example, the formulation for oral administration may include granules, powder, liquid, a tablet, a capsule, or dried syrup. For example, the formulation for parenteral administration may include an injectable solution or a composition for external application to the skin. The composition for external application to the skin includes the form of creams, lotions, or patches.

According to another embodiment of the present invention, there is provided a method of regenerating endothelial cells in a subject, the method including administering to the subject a pharmaceutical composition for regenerating endothelial cells that includes as an active ingredient of a DKK2 protein or a polynucleotide encoding the DKK2 protein in an effective amount for the regeneration of endothelial cells.

As used herein, the term "subject" refers to a subject with an illness that needs to be treated. The subject may be a subject with injured endothelial cells (endothelial dysfunction). The endothelial cell may be an endothelial cell of a penile erectile tissue, for example, including a corpus cavernosum endothelial cell and a penile vascular endothelial cell.

Endothelial dysfunction may be caused by dyslipidemia including hypercholesterolemia, diabetes mellitus, high blood pressure, cavernous nerve injury, or combinations thereof. The subject may be a mammal. For example, the subject includes human, a non-human primate, a rat, a mouse, a dog, a cat, a horse, or a cow.

The term "effective amount" used herein refers to an amount required to promote the regeneration of the endothelial cells in case when the composition is administered into a subject, compared with the case when it is not administered. The effective amount for the regeneration of endothelial cells may vary depending on a variety of factors or medical situations, including the type or severity of diseases, age or gender of patients, patient's responses to the medicine, treatment period, type or route of administration, excretion or metabolism of the medicine, or drug interactions, etc., Moreover, the term "effective amount" may include optimal dosage of the medicine to maximize treatment effect and to minimize the unwanted effect. Considering what was described above, the effective amount to regenerate endothelial cells may be determined by one of ordinary skill in the art. Thus, the effective amount may be, for example, in the range of 0.00001 mg/kg to 1000 mg/kg, 0.00001 mg/kg to 100 mg/kg, 0.00001 mg/kg to 10 mg/kg, 0.00001 mg/kg to 1 mg/kg, 0.0001 mg/kg to 1000 mg/kg, 0.001 mg/kg to 1000 mg/kg, 0.01 mg/kg to 1000 mg/kg, 0.1 mg/kg to 1000 mg/kg, 1 mg/kg to 1000 mg/kg, 10 mg/kg to 1000 mg/kg, or 100 mg/kg to 1000 mg/kg.

In this embodiment, the pharmaceutical composition including an active ingredient of a DKK2 protein or a polynucleotide encoding the DKK2 gene for generation of endothelial cells is the same as described above.

In the present embodiment, the administering process includes administration via a certain route enabling the pharmaceutical composition to reach penile erectile tissues. The administration route includes oral administration, intra-arterial injection, intravenous injection, penile injection including intracavernous injection, subcutaneous injection, intranasal administration, transbronchial administration, and intramuscular injection. For example, the administration includes administration of the composition in the form of an injectable solution via local injection into corpus cavernosum or a blood vessel. In addition, the administration route may be transdermal administration. For example, the transdermal administration may be performed by applying on skin a composition for external application to the skin, in the form of cream, lotion, or a patch, etc.

According to another embodiment of the present invention, there is provided a method of preventing or treating erectile dysfunction of a subject, the method including administering to a subject a pharmaceutical composition for preventing or treating erectile dysfunction that includes as an active ingredient of a DKK2 protein or a polynucleotide encoding the DKK2 protein in an effective amount for the treatment of erectile dysfunction.

As used herein, the term "subject" refers to a subject with an illness that needs to be treated. The subject may be one with erectile dysfunction or a subject likely to have erectile dysfunction. Erectile dysfunction may be caused by dyslipidemia (including hypercholesterolemia), diabetes mellitus, high blood pressure, cavernous nerve injury, or, combinations thereof. The subject may be a mammal. For example, the subject may be at least one selected from the group consisting of a human, a non-human primate, a rat, a mouse, a dog, a cat, a horse, and a cow.

The term "effective amount" used herein refers to an amount required to significantly improve penile erection, for example, improving an erection and/or increasing a lasting time of an erection in case when the composition is administered into a subject, compared with the case when it is not administered. The effective amount for the treatment of penile erection may vary depending on a variety of factors or medical situations, including the type or severity of diseases, age or gender of patients, patient's responses to the medicine, treatment period, type or route of administration, excretion or metabolism of the medicine, or drug interactions, etc., Moreover, the term "effective amount" may include optimal dosage of the medicine to maximize treatment effect and to minimize the unwanted effect. Considering what was described above, the effective amount to improve penile erection may be determined by one of ordinary skill in the art. Thus, the effective amount may be, for example, in the range of 0.00001 mg/kg to 1000 mg/kg, 0.00001 mg/kg to 100 mg/kg, 0.00001 mg/kg to 10 mg/kg, 0.00001 mg/kg to 1 mg/kg, 0.0001 mg/kg to 1000 mg/kg, 0.001 mg/kg to 1000 mg/kg, 0.01 mg/kg to 1000 mg/kg, 0.1 mg/kg to 1000 mg/kg, 1 mg/kg to 1000 mg/kg, 10 mg/kg to 1000 mg/kg, or 100 mg/kg to 1000 mg/kg.

In this embodiment, the pharmaceutical composition for preventing or treating erectile dysfunction that includes as an active ingredient of a DKK2 protein or a polynucleotide encoding the DKK2 protein is the same as described above.

In the method according to the present embodiment, the administering process includes administration via a certain route enabling the pharmaceutical composition to reach penile erectile tissues. The administration route includes oral administration, intra-arterial injection, intravenous injection, penile injection including intracavernous injection, subcutaneous injection, intranasal administration, transbronchial administration, and intramuscular injection.

For example, the administration may include administration of the composition in the form of an injectable solution via local injection into corpus cavernosum or a blood vessel. In addition, the administration route may be transdermal administration. For example, the transdermal administration may be performed by applying on skin a composition for external application to the skin, in the form of cream, lotion, or a patch, etc.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of treating erectile dysfunction of a subject, the method comprising administering to the subject a pharmaceutical composition for treating erectile dysfunction which comprises as an active ingredient a Dickkopf-related protein 2 (DKK2) or a polynucleotide encoding the DKK2 protein in an effective amount for the treatment of erectile dysfunction, wherein the subject is a human male suffering from erectile dysfunction, wherein the step of administering comprises administering the pharmaceutical composition into a penis of the subject, and wherein the erectile dysfunction is caused by diabetes mellitus, wherein the step of administering comprises administering the pharmaceutical composition into a corpus cavernosum penis of the subject.

2. The method of claim 1, wherein the effective amount is 0.01 mg/kg to 10 mg/kg of body weight.

* * * * *